United States Patent
Hühn et al.

(10) Patent No.: US 10,568,339 B2
(45) Date of Patent: Feb. 25, 2020

(54) COFFEE PROCESS

(75) Inventors: Tilo Hühn, Schönenberg (CH); Roland Laux, Roggwil (CH)

(73) Assignee: ZUERCHER HOCHSCHULE FUER ANGEWANDTE WISSENSCHAFTEN, Waedenswil (CH)

( * ) Notice: Subject to any disclaimer, the term of this patent is extended or adjusted under 35 U.S.C. 154(b) by 943 days.

(21) Appl. No.: 13/141,846

(22) PCT Filed: Dec. 24, 2009

(86) PCT No.: PCT/IB2009/007883
§ 371 (c)(1),
(2), (4) Date: Sep. 19, 2011

(87) PCT Pub. No.: WO2010/073114
PCT Pub. Date: Jul. 1, 2010

(65) Prior Publication Data
US 2012/0027900 A1  Feb. 2, 2012

Related U.S. Application Data

(60) Provisional application No. 61/140,842, filed on Dec. 24, 2008.

(51) Int. Cl.
*A23F 5/00* (2006.01)
*A23F 5/24* (2006.01)
(Continued)

(52) U.S. Cl.
CPC ............. *A23F 5/02* (2013.01); *A23F 5/04* (2013.01); *A23F 5/08* (2013.01); *A23F 5/26* (2013.01);
(Continued)

(58) Field of Classification Search
CPC .......... A23F 5/486; A23F 5/243; A23F 5/405; A23F 5/505; A23F 5/26; A23F 5/262; A23F 5/48; A23F 5/28; A23F 5/285; A23F 5/36; A23F 3/426; A23F 5/46; A23F 5/483; A23F 5/32; A23F 5/04; A23F 5/18; A23F 5/08; A23F 5/34; A23F 5/10;
(Continued)

(56) References Cited

U.S. PATENT DOCUMENTS 3,244,530 A     4/1966  Byer et al.
3,482,987 A  *  12/1969  Feldbrugge ............... A23F 5/16
                                              426/432
(Continued)

FOREIGN PATENT DOCUMENTS

EP    0 240 067 A2    10/1987
EP    1 595 458 A1    11/2005
(Continued)

OTHER PUBLICATIONS

JP 2003204757 A, Hisamori et al. Derwent Abstract. English Translation.*

*Primary Examiner* — Hong T Yoo
(74) *Attorney, Agent, or Firm* — Kilyk & Bowersox, P.L.L.C.

(57) ABSTRACT

Methods and/or processes for obtaining coffee extracts and/or processing coffee beans. In certain embodiments, improved methods and/or processes for producing desirable and usable extracts from coffee beans which can be used for instant coffee type powders or liquids, for example. In certain other embodiments, improved coffee extraction techniques which permit or allow retainment or capture of desirable levels of aroma products and/or bio-actives from coffee beans.

22 Claims, 6 Drawing Sheets

(51) Int. Cl.
    *A23F 5/02*     (2006.01)
    *A23F 5/26*     (2006.01)
    *A23F 5/50*     (2006.01)
    *A23F 5/28*     (2006.01)
    *A23F 5/04*     (2006.01)
    *A61K 36/74*     (2006.01)
    *A23F 5/32*     (2006.01)
    *A23F 5/48*     (2006.01)
    *A23F 5/08*     (2006.01)
    *A23L 33/105*     (2016.01)

(52) U.S. Cl.
    CPC ................ *A23F 5/285* (2013.01); *A23F 5/32* (2013.01); *A23F 5/486* (2013.01); *A23F 5/505* (2013.01); *A23L 33/105* (2016.08); *A61K 36/74* (2013.01)

(58) Field of Classification Search
    CPC ... A23F 5/105; A23F 3/18; A23F 5/24; A23F 5/30; A23F 5/00; A23V 2250/2108; A23L 1/234
    See application file for complete search history.

(56) References Cited

U.S. PATENT DOCUMENTS

| | | | | |
|---|---|---|---|---|
| 3,652,292 A | * | 3/1972 | Bach | A23F 5/08 |
| | | | | 426/385 |
| 4,045,586 A | | 8/1977 | Howland et al. | |
| 4,100,305 A | * | 7/1978 | Gregg | 426/385 |
| 4,281,023 A | | 7/1981 | Pyves | |
| 4,474,820 A | * | 10/1984 | Hawes et al. | 426/387 |
| 4,794,010 A | | 12/1988 | Jones et al. | |
| 2002/0160067 A1 | | 10/2002 | Zapp et al. | |
| 2007/0231443 A1 | * | 10/2007 | Goto | A21D 2/00 |
| | | | | 426/594 |

FOREIGN PATENT DOCUMENTS

| | | | | |
|---|---|---|---|---|
| GB | 1 265 206 | | 3/1972 | |
| GB | 2 057 849 | | 4/1981 | |
| JP | 2003 204757 | | 7/2003 | |
| JP | 2003204757 A | * | 7/2003 | ............. A23F 5/28 |
| JP | 2005 087122 | | 4/2005 | |
| WO | 95/11595 A1 | | 5/1995 | |

* cited by examiner

COFFEE PROCESS

RELATED APPLICATION DATA

This is the U.S. national stage of International application PCT/IB2009/007883, filed Dec. 24, 2009 designating the United States and claiming the benefit of priority of U.S. Patent Application No. 61/140,842, filed on Dec. 24, 2008 and similarly titled. The entirety of such application is hereby incorporated by reference.

FIELD OF THE INVENTION

This invention relates to methods and/or processes for processing coffee beans and/or obtaining coffee extracts. In certain embodiments, this invention relates to improved methods and/or processes for producing usable extracts from coffee beans which can be used for instant coffee type powders or liquids, for example. This invention further relates to the improved techniques for extraction of aroma products and/or bio-actives from coffee beans.

BACKGROUND OF THE INVENTION

Although coffee extraction methods and/or processes have been known for approximately a century, modern extraction methods or techniques remain deficient in various respects. In this regard, during prior art or conventional coffee extraction techniques, certain commercially useful and/or valuable coffee by-products are lost or wasted. For example, aromatization and/or bio-active products or particles are often lost or at least not captured or retained at desirable levels. Because such products can be used in the production or enhancement of other commercially valuable food products (including that such aromatization products can be added back to coffee powders or liquids), for example, it would be desirable to achieve a method or process for coffee bean extraction which improves the retainment or capture rate of such coffee by-products. Moreover, it would be desirable to capture such by-products at a time and in a manner which did not result in undesirable levels of degradation.

In addition to the above drawbacks, prior known coffee extraction techniques can result in coffee powders or liquids (e.g., for use as or in so-called "instant coffee" products) which possess undesirable flavor characteristics. For example, such coffee extraction products, produced by prior art techniques, often contain excess or undesirable quantities of lipids which, in turn, result in coffee products which are less flavorful than preferred (and which may be rancid in flavor, for example). Improved coffee extraction techniques or processes which reduce the presence of such undesirable flavors (such as by decreasing the amount of resulting lipids in coffee end products) are desired.

In view of the above enumerated drawbacks and/or desires for improvements in the art, it is a purpose of the herein described invention to address one or more of such drawbacks and/or desires as well as, or in the alternative, other needs which will become more apparent to the skilled artisan once given the present disclosure.

SUMMARY OF CERTAIN EMBODIMENTS OF THE INVENTION

Generally speaking, the present invention is directed to improved techniques for processing coffee beans and, in particular, for extracting useful products from coffee beans. In certain non-limiting embodiments, the invention is directed to methods and/or processes of extracting products useful for coffee powders and/or liquids (e.g., for use as or with instant coffee type products or as coffee flavor additives). In certain other non-limiting, example embodiments, the invention is directed towards methods and/or processes for extracting aromatics or bio-actives or other desirable by-products from coffee beans for use in one or more food industries or other commercial-type applications (including, for example, for addition to coffee powders and the like).

In at least one embodiment of the invention, therein is provided a method of processing coffee beans comprising:
  breaking or cracking whole coffee beans;
  adding water to said broken or cracked coffee beans to form a suspension or mixture;
  grinding the cracked coffee beans;
  adding the ground coffee beans to a heat exchanger;
  optionally removing aromatics via an aroma evaporator;
  separating solid material from liquid in a decanting step;
  performing an additional separation step to separate solids and/or lipids and/or aromatics and/or liquids;
  subjecting certain coffee extraction products to an evaporation step and/or a lyophilization step; and
  obtaining one or more of the following products: coffee powder; coffee liquid; aromatics; polyphenols; and bio-actives.

In an alternative embodiment of the invention, therein is provided a method of processing coffee beans comprising:
  selecting and blending whole, unroasted coffee beans;
  roasting the coffee beans;
  blending the coffee beans with water and heat;
  breaking or cracking the coffee beans;
  grinding or milling the cracked coffee beans;
  performing an extraction step on the ground or milled coffee beans with heat and under pressure;
  performing a vacuum de-aeration or evaporation step on the coffee beans;
  optionally removing aromatics in an aroma recovering step;
  separating solid material from liquid in a decanting step;
  performing an additional separation step to separate solids and/or lipids and/or aromatics and/or liquids;
  subjecting certain coffee extraction products to an evaporation step and/or a lyophilization step; and
  obtaining one or more of the following products: coffee powder; coffee liquid; aromatics; polyphenols; and bio-actives.

In one embodiment of a coffee extraction process according to the subject invention, after roasting and fine grinding the coffee beans (e.g., preferably, but not necessarily directly after roasting), an extraction with water takes place at approximately 90° C. Afterwards, a vacuum evaporator is used which removes approximately 20% v/v of steam and/or volatiles (often lost in prior art coffee processing techniques). Such components may thereafter be used for soluble or instant type coffee or as an aromatizing-agent for other products (food or non-food). Thereafter, in at least one embodiment, separation of solids from the liquid phase takes place in a decanting step. After such decanting step, the liquid phase contains water-soluble flavors and polyphenols as well as certain useful fats or lipids. Following the decanting step, a three-phase separation step can be utilized to perform further separations to obtain a mixture of water-soluble polyphenols and/or water-soluble flavors which, if sprayed or dried, contain desirably low amounts of lipids (as compared to prior art processes) and thus possess desirable flavor characteristics (e.g., with reduced presence of rancid flavors).

In at least one embodiment of the invention, a roasting step is performed for approximately 5-12 minutes at between 180-230 degrees C. During such step, a reduction in water content from approximately 10-12% to approximately 1.5-3% occurs.

In at least one embodiment of the invention, in a second blending step, the second blending step is performed using water and heat at approximately 90 degrees C.

In a further embodiment of the subject coffee processing invention, a cracking and/or breaking step is performed using a perforated disk mill. In such or other embodiments, a milling or grinding step is thereafter performed using a toothed colloid mill.

In at least one embodiment of the subject invention, the extraction step is performed for approximately 2-6 minutes at approximately 90 degrees C. and at pressure of approximately 2-3 bars. In this or other embodiments, a vacuum de-aerator step is performed under pressure at approximately 100 mbars.

In an optional aroma (or aromatic) recovering step in one or more of the herein described embodiments, an absorber column may be used as well as reverse osmosis techniques and/or the addition of ethanol. Collected aromatics may then be reconstituted and/or packaged.

In yet an additional embodiment of the subject invention, after a first decanting step in which solids are separated from a liquid phase, a second decanting step may optionally be performed. Such second decanting step may thereafter be followed by a three-phase separation step.

In certain non-limiting embodiments of the subject invention, coffee extraction products may be subjected to one or more product preservation or drying steps including evaporation and/or spray drying and/or freeze drying steps. Afterwards, such products may be packaged for commercial or manufacturing use (e.g., for use in manufacturing food stuffs or as additives therefore).

In certain non-limiting embodiments of the invention, it is an object to obtain early recovery of aroma (or aromatic) components (e.g., for prevention of degradation) and/or to achieve separation of the fat phase with fat-soluble flavor materials to reduce the risk of typically undesirable rancid type flavors occurring or being present.

In a further embodiment according to or in combination with any one of the preceding or following embodiments, a method is provided further including a step wherein after roasting and fine grinding steps, the coffee beans are subjected to an extraction with water at a temperature selected from between approximately 80-100° C.

In a further embodiment according to or in combination with any one of the preceding or following embodiments, a method is provided further including a step wherein after roasting and fine grinding steps, the coffee beans are subjected to an extraction with water at a temperature of approximately 90° C.

In a further embodiment according to or in combination with any one of the preceding or following embodiments, a method is provided further including a step wherein after the extraction with water step, a vacuum evaporator is used to remove approximately 20% v/v of steam and/or volatiles.

In a further embodiment according to or in combination with any one of the preceding or following embodiments, a method is provided further including a step wherein coffee components obtained are used for soluble or instant type coffee or as an aromatizing agent.

In a further embodiment according to or in combination with any one of the preceding or following embodiments, a method is provided further including a step wherein separation of solids from the liquid phase takes place in a decanting step.

In a further embodiment according to or in combination with any one of the preceding or following embodiments, a method is provided further wherein after a decanting step, the liquid phase contains water-soluble flavors and polyphenols as well as fats or lipids In a further embodiment according to or in combination with any one of the preceding or following embodiments, a method is provided wherein following the decanting step, a three-phase separation step is performed to obtain further separations to obtain a mixture of water-soluble polyphenols and/or water-soluble flavors which, when sprayed or dried, contain low amounts of lipids.

In a further embodiment according to or in combination with any one of the preceding or following embodiments, a method is provided further including a step wherein a roasting is performed for approximately 5-12 minutes at between 180-230 degrees C.

In a further embodiment according to or in combination with any one of the preceding or following embodiments, a method is provided further including a step wherein during a roasting, a reduction in water content from approximately 10-12% to approximately 1.5-3% occurs.

In a further embodiment according to or in combination with any one of the preceding or following embodiments, a method is provided wherein in a second blending step, the second blending step is performed using water and heat at approximately 90 degrees C.

In a further embodiment according to or in combination with any one of the preceding or following embodiments, a method is provided further including a step wherein a cracking and/or breaking step is performed using a perforated disk mill.

In a further embodiment according to or in combination with any one of the preceding or following embodiments, a method is provided further including a step wherein a milling or grinding step is performed using a toothed colloid mill.

In a further embodiment according to or in combination with any one of the preceding or following embodiments, a method is provided further including a step wherein an extraction step is performed for approximately 2-6 minutes at approximately 90 degrees C. and at pressure of approximately 2-3 bars.

In a further embodiment according to or in combination with any one of the preceding or following embodiments, a method is provided further including a step wherein a vacuum de-aerator step is performed under pressure at approximately 100 mbars.

In a further embodiment according to or in combination with any one of the preceding or following embodiments, a method is provided further including a step wherein in an optional aromatic recovery step, an absorber column is used.

In a further embodiment according to or in combination with any one of the preceding or following embodiments, a method is provided further including a step wherein in an optional aromatic recovery step, reverse osmosis techniques are used.

In a further embodiment according to or in combination with any one of the preceding or following embodiments, a method is provided further including a step wherein in an optional aromatic recovery step, ethanol is added.

In a further embodiment according to or in combination with any one of the preceding or following embodiments, a method is provided further including a step wherein collected aromatics are reconstituted and/or packaged.

In a further embodiment according to or in combination with any one of the preceding or following embodiments, a method is provided further including a step wherein after a first decanting step in which solids are separated from a liquid phase, a second decanting step is performed.

In a further embodiment according to or in combination with any one of the preceding or following embodiments, a method is provided further including a step wherein a second decanting step is followed by a three-phase separation step.

In a further embodiment according to or in combination with any one of the preceding or following embodiments, a method is provided further including a step wherein coffee extraction products are treated with evaporation steps and/or spray drying steps and/or freeze drying steps.

In a further embodiment according to or in combination with any one of the preceding or following embodiments, a method is provided further including a step wherein separation of the fat phase from fat-soluble flavor materials is performed.

In a further embodiment according to or in combination with any one of the preceding or following embodiments, a method is provided further including a step wherein products for instant coffee products or coffee flavor additives are obtained.

In a further embodiment according to or in combination with any one of the preceding or following embodiments, a method is provided further including a step wherein aromatics or bio-actives are obtained.

Certain examples of the invention are now below described with respect to certain non-limiting embodiments thereof as illustrated in the following drawings wherein:

DETAILED DESCRIPTION OF CERTAIN EMBODIMENTS

For a more complete understanding of the present invention, reference is now made to the following description of various illustrative and non-limiting embodiments thereof, taken in conjunction with the accompanying drawings in which like reference numbers indicate like features.

Figure 1:
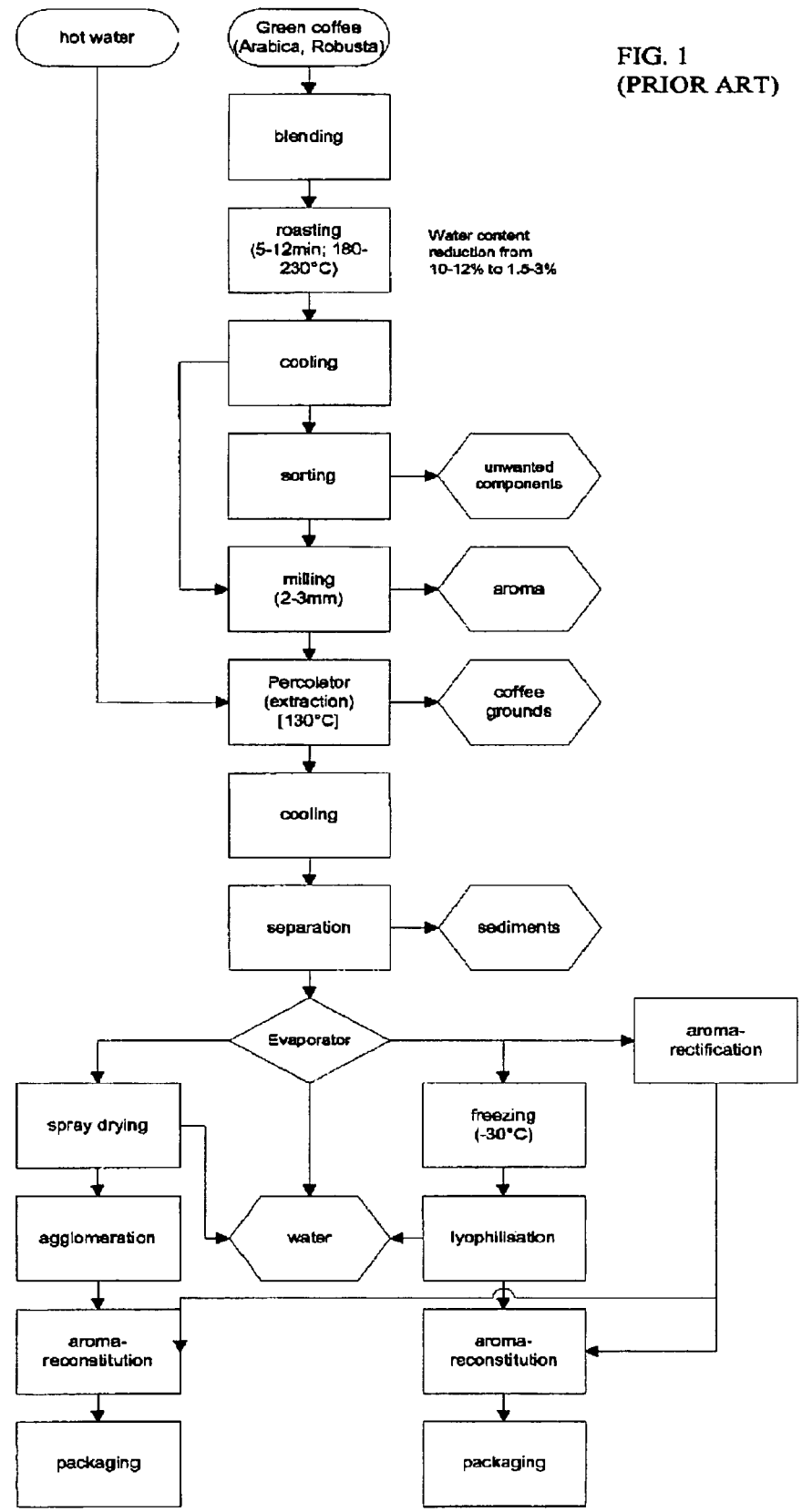
FIG. 1 illustrates a flow chart depicting a prior art method for processing coffee beans.

FIG. 1, as indicated by its label, illustrates a prior art method for processing coffee beans which the techniques and/or methods described herein are intended to improve and/or replace.

Example 1

Figure 2:
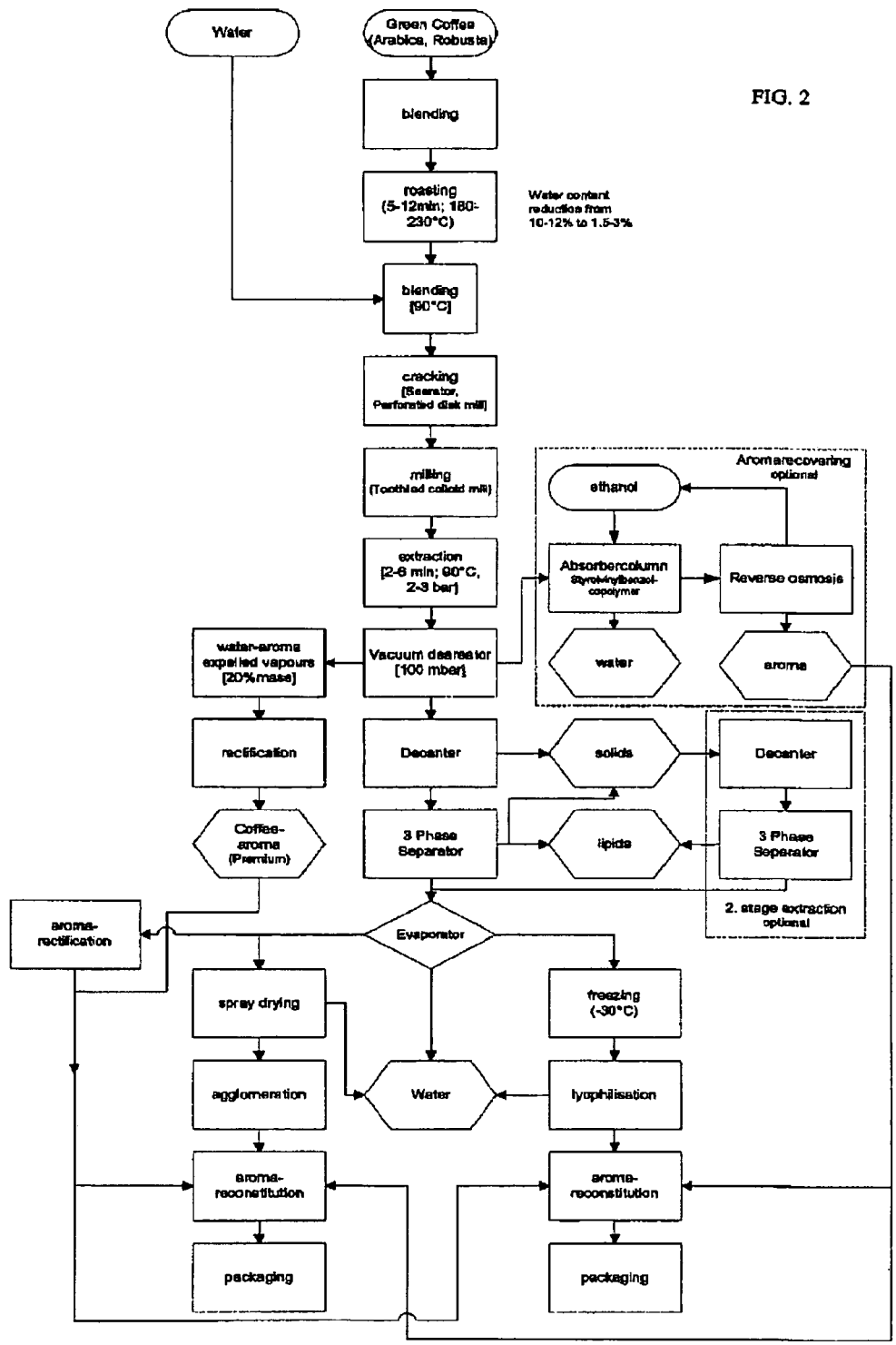
FIG. 2 illustrates a flow chart depicting one non-limiting embodiment of a method of processing coffee beans according to the subject invention.
Figure 3:
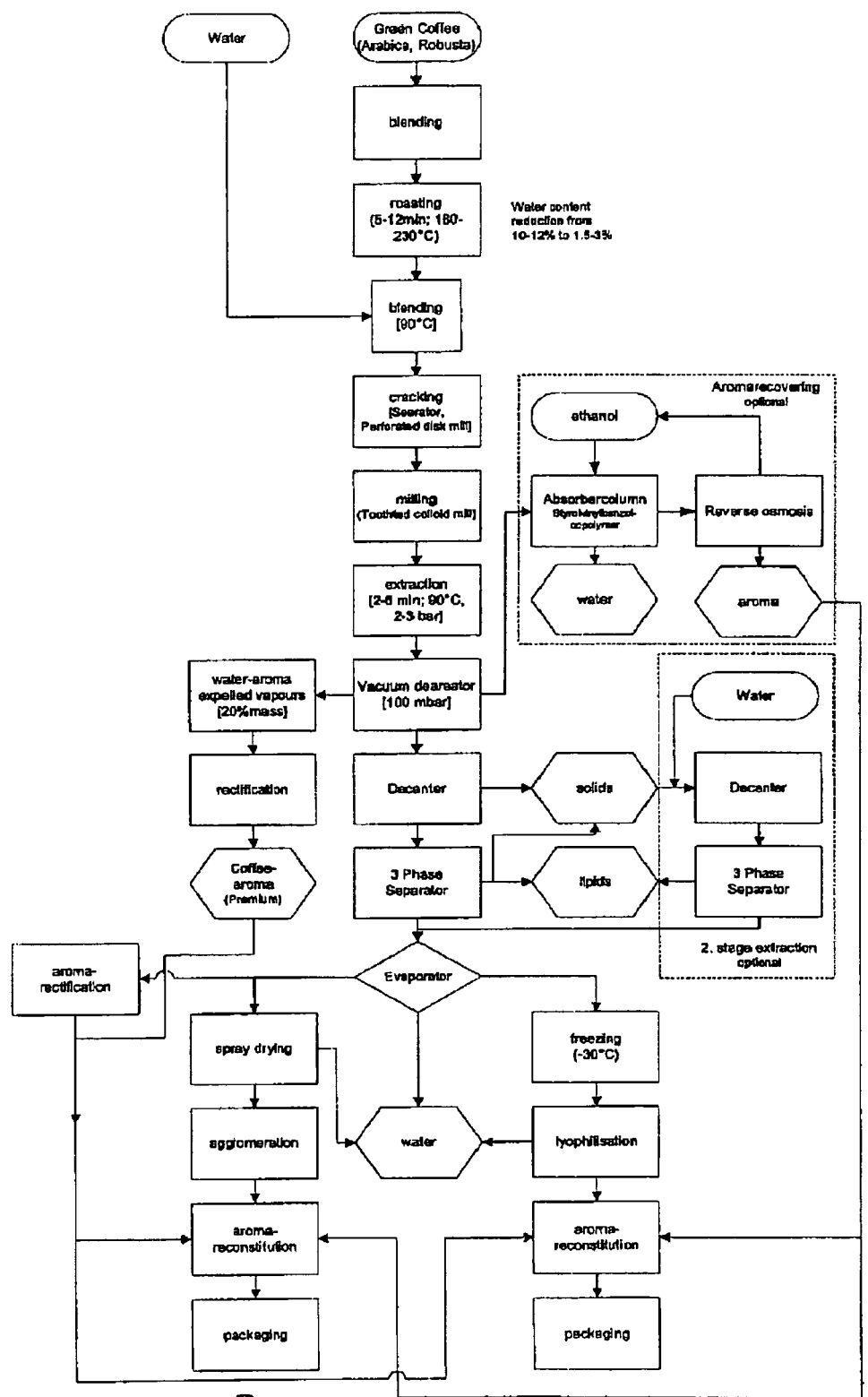
FIG. 3 schematically illustrates an embodiment of an alternative coffee processing technique according to the subject invention.
Figure 4:
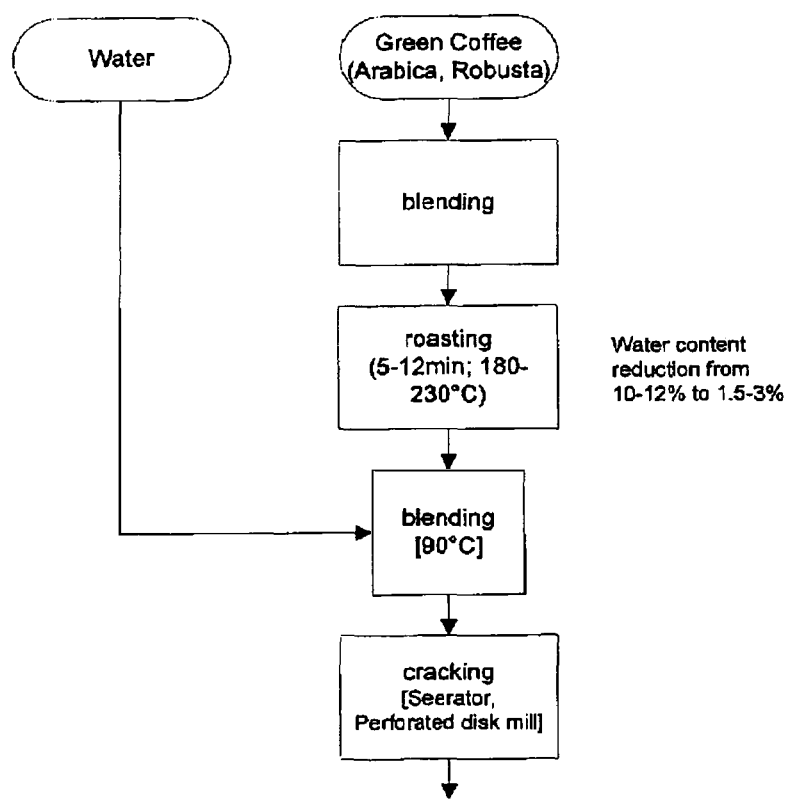
FIG. 4 schematically illustrates certain steps in the embodiment of the coffee processing technique illustrated in FIG. 3.
Figure 5:
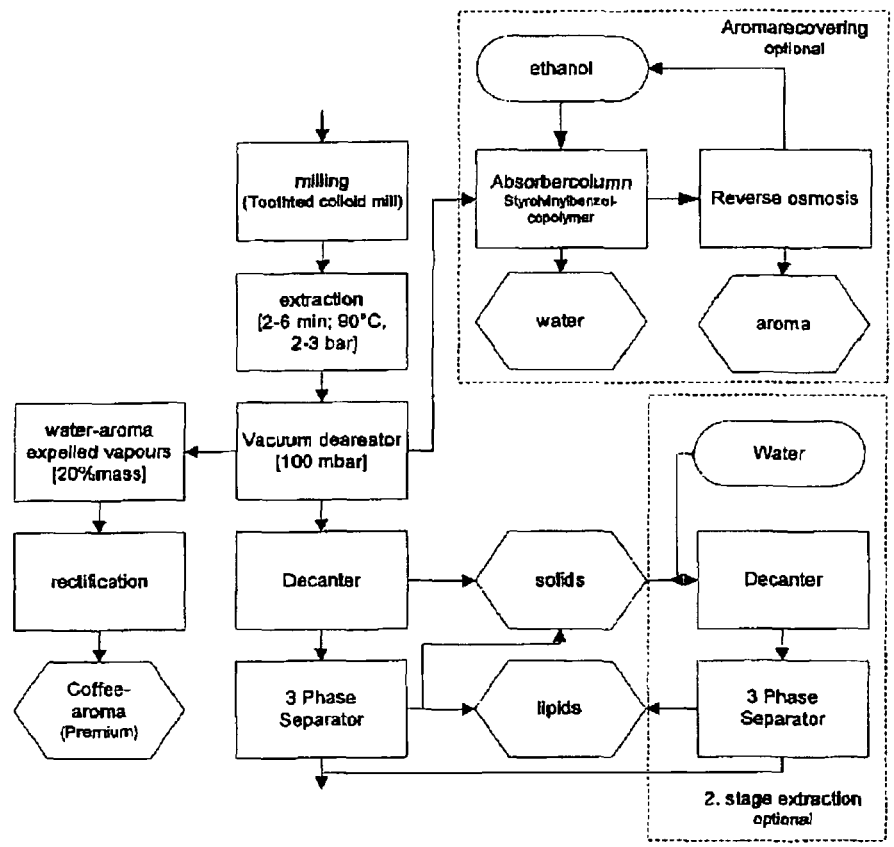
FIG. 5 schematically illustrates certain steps in the embodiment of the coffee processing technique illustrated in FIG. 3.
Figure 6:
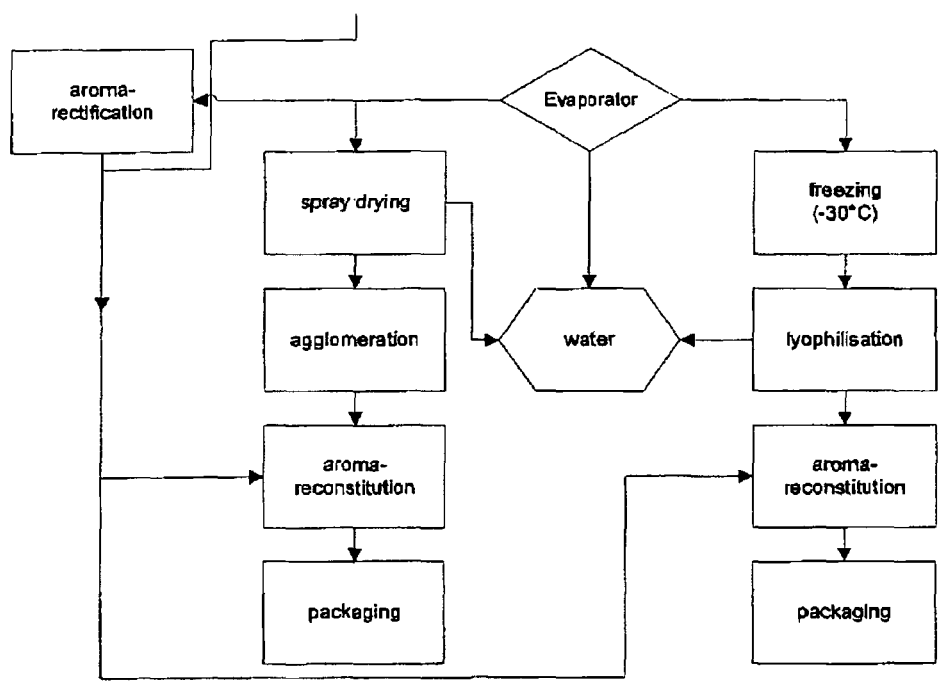
FIG. 6 schematically illustrates certain steps in the embodiment of the coffee processing technique illustrated in FIG. 3.

Referring initially to FIG. 2, an exemplar embodiment of a technique for processing coffee beans is illustrated therein (i.e., as a flow chart illustrating the various steps in one example inventive method of processing coffee beans). As illustrated in FIG. 2, the subject coffee processing technique generally begins with the selection and blending of whole coffee beans to obtain desired flavor characteristics (based upon selecting beans according to regional taste characteristics of coffee beans, for example). After the beans are initially selected and blended, the beans are roasted for between 5-12 minutes at a temperature of between approximately 180-230 degrees C. In particular, this reduces the water content of the beans to levels desirable and/or acceptable for further processing (e.g., from approximately 10-12% water content to approximately 1.5-3% water content). Afterwards, the beans may be optionally blended again with the addition of water and heat at approximately 90 degrees C.

In the illustrated embodiment, after the initial bean processing steps, the beans are cracked or broken into pieces or particles possibly or preferably using a perforated disk mill (e.g., of conventional, known construction). Thereafter, the coffee bean particles or pieces are subjected to a further particle size reduction step (e.g., a grinding or milling step) which is preferably (but not necessarily) performed using a toothed colloid mill.

Once a desired coffee bean particle size is achieved, an extraction step is performed on the coffee bean particles. This step is performed for approximately 2-6 minutes at approximately 90 degrees C. and at a pressure of approximately 2-3 bars. Afterwards, a vacuum evaporator is used which removes approximately 20% v/v of steam and/or volatiles (often lost in prior art coffee processing techniques) e.g., performed under pressure at approximately 100 mbars. Such removed components may thereafter be used for soluble or instant type coffee or as an aromatizing agent for other products (food or non-food).

Thereafter, in the illustrated embodiment, separation of solids from the liquid phase takes place in a decanting step (which typically at least removes the larger solid particles). After such decanting step, the liquid phase contains water-soluble flavors and polyphenols as well as certain useful fats or lipids.

Following the decanting step in this exemplar embodiment, a three-phase separation step is utilized to perform further separations to obtain a mixture of water-soluble polyphenols and/or water-soluble flavors which, when or if sprayed or dried, contain desirably low amounts of lipids (as compared to prior art processes) which thus possess desirable flavor characteristics (e.g., reduced rancid flavors).

In one or more optional steps illustrated in FIG. 2, an aroma recovery step may be performed, for example. In such step as illustrated, an absorber column may be used as well as reverse osmosis techniques and/or the addition of ethanol. Collected aromatics obtained during this step may then be reconstituted and/or packaged. In a second optional step (also as illustrated), after a first decanting step in which solids are separated from a liquid phase, a second decanting step is performed. Such second decanting step may thereafter (also optionally) be followed by a three-phase separation step.

In one alternative embodiment of a coffee extraction process according to the subject invention (which departs from the process step order illustrated in FIG. 2), after roasting and fine grinding the coffee beans (e.g., preferably, but not necessarily directly after roasting), an extraction with water takes place at approximately 90° C. Afterwards, as with the above described embodiment, a vacuum evaporator is used to remove steam and/or volatiles. Thereafter, and similar to the embodiment described in FIG. 2, separation of solids from the liquid phase takes place in a decanting step and then proceeds generally in accord with the steps illustrated in such figure (with a three-phase separation step, optional second decanting step, etc.).

Performing the process illustrated in FIG. 2 or the alternative process described above (but not pictured in the figure), one or more of the following products are obtained: coffee powder; coffee liquid; aromatics; polyphenols; and bio-actives. Such products, for preservation or for the purpose of packaging, may be subjected to one or more product preservation or drying steps (at the end of the illustrated and/or herein described methods or processes or during intermediate phases of such methods or processes) including evaporation and/or spray drying and/or freeze drying steps (according to the steps depicted in the flowchart of FIG. 2 or in accordance with conventional spray drying or freeze drying methods). Afterwards, such products may be packaged for commercial or manufacturing use (e.g., for use as additives or in manufacturing food stuffs).

Example 2

Turning now to FIGS. 3 through 6, a second example (non-limiting) embodiment of a technique for processing coffee beans is illustrated therein. As illustrated in these figures, in the first steps of this example embodiment, coffee bean blending, roasting and cracking steps are performed. Certain example steps in such a process are set forth as follows:

Blending: Coffee bean types (e.g., beans selected from different varieties or from different origins) or combinations thereof are selected and mixed.

Roasting: In a roasting step, blended beans are heated for approximately 5-12 minutes at between 180 and 230 degrees Celsius. In this roasting step, roast aroma is formed.

Blending: In a second blending step (optionally performed at approximately 90 degrees Celsius), the beans are mixed with water and appropriate temperature (e.g., heat) is applied in preparation for the milling and extraction procedure. In certain (but not all) embodiments of the invention, this is the only step in which water is added. One exception (though there are others) is if an optional second extraction step is performed. In the other steps of the process, water can be recycled.

Cracking: In a cracking or breaking step, the coffee beans are broken in preparation for milling. After the cracking step, the broken or cracked beans may be transported by pumps to mills for grinding such as a toothed colloid or corundum stone mill (other mill types may, of course, be employed). Pre-cracking the beans prior to grinding reduces heat impact on the beans during grinding steps.

Milling: In at least one milling step, maceration of coffee beans (e.g., to particle sizes <10 μm) enables the solvent (water) to wet the coffee bean material through enlargement of the surface area. Sufficient wetting leads to a better extraction of the quality determining substances e.g. fat, aroma substances, and polyphenols.

Extraction: In an extraction step, pre-macerated coffee beans are extracted for approximately 2-6 minutes at approximately 90 degrees Celsius, at pressure (e.g., at approximately at 2-3 bars).

Vacuum deaeration: In a deaeration step, a stripping of approximately 20% (m/m) of expelled vapour is performed to increase the yield of sensitive aroma components (e.g. sulphur containing aroma substances which are character impact components for fresh extracted coffee). Moreover, a rectification or optional absorption step is performed which leads to a decreased degradation of aroma components.

Decanter: In a decanting step, solids are separated from the liquid phase by centrifugal forces. At this step, mainly the coarser or larger solids will be removed. The water/oil phase will be further processed by the next step. Optionally, the separated solids may be dried. An optional second decanting step with a further addition of water may also be performed to enhance the yield.

Separator: In a separation step, fine particles are removed from the liquid phase. In certain embodiments, this step separates oil (e.g., lipids with hydrophobic aroma components) and liquid phase components (e.g., coffee extract with hydrophilic aroma and polyphenol components). Optionally, in this step or an additional step, the concentration of the lipid phase in lyophilisated coffee can be reduced to decrease the risk of rancid or other undesirable flavor(s).

Evaporator: In at least one evaporation step, evaporation of excessive water from degreased coffee extract may be achieved. Together with the water, certain flavor compounds will also be evaporated and recovered. Polyphenols may also be concentrated in this step.

Spray drying/freezing: In at least one spray or freeze drying step, a production of the base for the instant product is obtained.

Aroma reconstitution: In at least one aroma reconstitution step, saved aroma fractions may be utilized. For example, aroma fractions may be added to products before packaging.

Water gained by decantation, separation, and evaporation (including water from the aroma recovery) in the above-described example processes, can be sterilized (or tyndalized to kill spores if necessary) with heat to prevent microorganism spoilage/propagation. Moreover, if needed the water can be deodorized using a vacuum de-aerator.

Once given the above disclosure, many other features, modifications, and improvements will become apparent to the skilled artisan. Such features, modifications, and improvements are therefore considered to be part of this invention, without limitation imposed by the example embodiments described herein. Moreover, any word, term, phrase, feature, example, embodiment, or part or combination thereof, as used to describe or exemplify embodiments herein, unless unequivocally set forth as expressly uniquely defined or otherwise unequivocally set forth as limiting, is not intended to impart a narrowing scope to the invention in contravention of the ordinary meaning of the claim terms by which the scope of the patent property rights shall otherwise be determined.

We claim:

1. A method of processing coffee beans comprising:
   selecting and blending whole, unroasted coffee beans;
   roasting the whole, unroasted coffee beans to obtain whole, roasted coffee beans;
   blending the whole, roasted coffee beans with water and under heat;
   subsequently, breaking or cracking the whole roasted coffee beans to obtain broken or cracked coffee beans, or breaking or cracking the whole roasted coffee beans and adding water to form a suspension or mixture;

grinding or milling the broken or cracked coffee beans, the suspension or mixture to obtain ground or milled coffee beans;

performing a first extraction on the ground or milled coffee beans with heat and under pressure;

subsequently, performing a first vacuum de-aeration or evaporation step on the coffee beans on which said first extraction was performed;

subsequently, recovering aroma components contained in vapor expelled in said first vacuum de-aeration or evaporation step;

separating solid material from a water/oil phase in a first decanting step, wherein the water/oil phase comprises: particles, an oil phase, and a water phase;

separating the water/oil phase into the particles, the oil phase comprising lipids with hydrophobic aroma components and the water phase comprising water-soluble flavors, water-soluble polyphenols and fats or lipids adapted to be maintained in the water phase, to obtain one or more coffee extraction products, wherein at least one of the coffee extraction products comprises the fats or lipids adapted to be maintained in the water phase;

subjecting at least the coffee extraction product comprising the fats or lipids adapted to be maintained in the water phase to a second evaporation in which excessive water is evaporated;

recovering flavor compounds evaporated in said second evaporation together with the water; and subsequently lyophilizing at least the coffee extraction product comprising the fats or lipids adapted to be maintained in the water phase to obtain, after adding the aroma components recovered in the first vacuum de-aeration or evaporation step and/or the flavor compounds recovered in the second evaporation step, coffee products.

2. A method of processing coffee beans according to claim 1 wherein the first extraction is performed with water at a temperature selected from between approximately 80-100° C.

3. A method of processing coffee beans according to claim 1 wherein the first extraction with water is performed at a temperature of approximately 90° C.

4. A method of processing coffee beans according to claim 2 wherein after the first extraction with water, a vacuum evaporator is used to remove approximately 20% v/v of steam and/or volatiles.

5. A method of processing coffee beans according to claim 1 wherein the coffee products obtained are used for soluble or instant type coffee or as an aromatizing agent.

6. A method of processing coffee beans according to claim 1, wherein subsequent to the first decanting step, a three-phase separation is performed.

7. A method of processing coffee beans according to claim 1, wherein subsequent to the second decanting step, a three-phase separation is performed.

8. A method of processing coffee beans according to claim 1, wherein the roasting of the whole, unroasted coffee beans, results in a reduction in water content of the beans from approximately 10-12% to approximately 1.5-3%.

9. A method of processing coffee beans according to claim 1, wherein the blending is performed at approximately 90 degrees C.

10. A method of processing coffee beans according claim 1, wherein said cracking or breaking is performed using a perforated disk mill.

11. A method of processing coffee beans according claim 1 wherein said grinding or milling is performed using a toothed colloid mill.

12. A method of processing coffee beans according to claim 1, wherein the first extraction is performed for approximately 2-6 minutes at approximately 90 degrees C. and at pressure of approximately 2-3 bars.

13. A method of processing coffee beans according to claim 1 wherein the first vacuum de-aeration is performed under pressure at approximately 100 mbars.

14. A method of processing coffee beans according to claim 1, wherein aroma components contained in said vapor expelled in said first vacuum de-aeration or evaporation are recovered in an absorber column.

15. A method of processing coffee beans according to claim 1, wherein aroma components contained in said vapor expelled in said first vacuum de-aeration or evaporation are recovered via reverse osmosis techniques.

16. A method of processing coffee beans according to claim 15, wherein ethanol is added subsequent to said reverse osmosis.

17. A method of processing coffee beans according to claim 15, wherein the aroma components removed are reconstituted and/or packaged.

18. A method of processing coffee beans according to claim 1, wherein after the first decanting step a second decanting step is performed.

19. A method of processing coffee beans according to claim 18 wherein the second decanting step is followed by a three-phase separation step as an additional separation step.

20. A method of processing coffee beans according to claim 1, wherein during the separating of the water/oil phase fats are separated from fat-soluble flavor materials.

21. A method of processing coffee beans according to claim 1, wherein the coffee products comprise coffee powder which is processed to instant coffee products or coffee flavor additives.

22. The method of claim 1, wherein the water is added prior to the breaking or cracking the whole coffee beans.

* * * * *